United States Patent [19]
Mehigan

[11] Patent Number: 5,171,316
[45] Date of Patent: Dec. 15, 1992

[54] VALVULOTOME

[75] Inventor: John T. Mehigan, Palo Alto, Calif.

[73] Assignee: Pilling Co., Fort Washington, Pa.

[21] Appl. No.: 657,081

[22] Filed: Feb. 19, 1991

[51] Int. Cl.⁵ .............................................. A61B 17/32
[52] U.S. Cl. .................................................. 606/159
[58] Field of Search ........................ 606/159, 170, 160; 604/22; 128/151

[56] References Cited

U.S. PATENT DOCUMENTS

| | | | |
|---|---|---|---|
| 4,493,321 | 1/1985 | Leather | 606/159 |
| 5,047,041 | 9/1991 | Samuels | 606/159 |
| 5,049,154 | 9/1991 | Quadri | 606/159 |

FOREIGN PATENT DOCUMENTS 2161707  1/1986  United Kingdom ................ 606/170

OTHER PUBLICATIONS

"Valvulotomy of Valves in the Saphenous Vein Graft Before Coronary Artery bypass" Mills et al. Jun. 1976.

Primary Examiner—Michael H. Thaler
Attorney, Agent, or Firm—Howson & Howson

[57] ABSTRACT

A valvulotome for surgically removing venous valves in order to convert a vein into an arterial bypass, comprises a thin, elongated, flexible wire of Nickel-Titanium alloy coated with PTFE and having a head secured to its distal end. The head has a single, narrow, laterally extending arm, with a blade edge facing in the proximal direction and extending transverse to the wire. The head also has a blunt tip projecting in the distal direction and laterally spaced from the wire axis. The head has a pair of edges which are oblique with respect to the wire axis and which converge toward each other so that the width of the head is continuously tapered from locations adjacent to the ends of the blade edge toward the tip. The head has a blunt element adjacent to the end of the blade edge farthest from the wire axis, with at least a portion of said blunt element extending proximally relative to said end of the blade edge. The maximum dimension of the head in the direction perpendicular to a plane defined by the blade edge and the wire axis is less than the maximum dimension of the head in the direction parallel to the blade edge.

6 Claims, 1 Drawing Sheet

VALVULOTOME

BRIEF SUMMARY OF THE INVENTION

This invention relates to surgery, and in particular to a valvulotome, i.e. a device used for disabling valve leaflets in a vein to enable the vein to be used as an arterial by-pass.

The invention is particularly adapted for in situ vein grafting, a surgical procedure used in the treatment of femoro-popliteal occlusive disease, a condition in which an artery in the patient's leg is blocked. In situ vein grafting is an operation in which a vein, typically but not necessarily the saphenous vein in the patient's leg, is modified to permit it to conduct blood in a direction opposite to the usual direction so that, when grafted to an occluded artery, it can serve as a by-pass vessel. In the modification of the vein, its side branches are closed off by ligation, and the one-way valves, several of which exist along the vein, are rendered inoperative by means of a valvulotome, which is used to cut the valve leaflets so that they can no longer prevent blood flow in directions opposite to the normal flow of blood toward the heart.

A typical valvulotome is the so-called "retrograde valvulotome", which consists of an elongated rod or wire having an L-shaped distal end with a bulbous tip and a blade, located between the bulbous tip and the elongated portion of the rod and facing in the proximal direction. The distal end of the valvulotome is passed through a valve and the instrument is then pulled in the reverse direction, causing the blade to cut through a valve leaflet.

Difficulties are occasionally encountered in passing valvulotomes through veins when the valvulotomes have conventionally designed cutting heads. Conventionally designed valvulotome cutting heads also occasionally cause damage to vein walls and to side branches, or tend to become caught in side branches. Another problem encountered in the use of conventional valvulotomes is the difficulty of controlling the rotational position of the cutting head at the distal end of the instrument by rotating the handle at the proximal end of the instrument, due to twisting of the wire which connects the handle and the cutting head. Other problems are encountered in axial positioning of the cutting head.

One solution to the problem of controlling rotational positioning of a valvulotome is to provide a cutting head having multiple blades which simultaneously cut through the valve cusps of a vein. The single bladed valvulotome is still preferred, however, by a significant number of surgeons. The problem of controlling rotational position of a single bladed valvulotome has also been addressed by the use of a fiberoptic angioscope to monitor the cutting of valve leaflets. The angioscope is introduced at the upper portion of the vein while the valvulotome is introduced through the lower portion. The distal end of the angioscope follows the valvulotome cutting head through the vein as the valves are cut sequentially, beginning with the uppermost valve, and proceeding toward the lowermost valve. While angioscope monitoring is useful in insuring complete cutting of the valve cusps, unfortunately it does not solve the problem of damage to vein walls and side branches caused by conventional single-bladed valvulotomes.

The foregoing problems are addressed by the valvulotome according to this invention. The new valvulotome preferably comprises a thin, elongated, flexible wire having a head secured to its distal end, the head having a single, narrow, laterally extending arm, with a blade edge facing in the proximal direction and extending in a direction transverse to said axis. The head also has a blunt tip projecting in the distal direction. The head is shaped so that its width, measured in the plane defined by the blade edge and the wire axis, is continuously tapered from locations adjacent to the ends of said blade edge toward the tip, the tapered portion having a short radius of curvature at the tip, short radii of curvature at said locations adjacent to the ends of the blade edge, and longer radii of curvature in the portions of the head extending from said locations toward the tip.

Preferably, the blunt tip is laterally spaced from the wire axis, and the head has a pair of edges, which are oblique with respect to the wire axis and which are both located in the plane defined by the blade edge and wire axis, and converging toward the tip. The maximum dimension of the head in the direction perpendicular to the blade-edge/wire axis plane is preferably less than the maximum dimension of the head in the direction parallel to the blade edge.

The valvulotome head also preferably has a blunt element located adjacent to the end of said blade edge farthest from the wire axis, with at least a portion of the blunt element extending proximally relative to said end of the blade edge.

In the preferred embodiment of the valvulotome, the wire is composed of a Nickel-Titanium alloy, and is coated with polytetrafluoroethylene.

In brief, it is the principal object of this invention to provide an valvulotome which is capable of being monitored through a fiberoptic angioscope, and which passes through a vein easily and atraumatically. It is also an object of the invention to provide an valvulotome which is simple, reliable, easily manufactured and easily used. Other objects, advantages and details of the invention will be apparent from the following description, when read in conjunction with the drawings.

DETAILED DESCRIPTION

The preferred valvulotome comprises a wire 4 composed of high tensile strength Nickel-Titanium alloy having a sheath 6 of polytetrafluoroethylene (PTFE), the smoothness of which aids the passage of the wire through the vein. Nickel-Titanium alloy is a desirable material for wire 4 because it is extremely flexible, yet capable of transmitting adequate torque from the handle to the cutting head through a distance of one meter or more.

Although the dimensions of the instrument can vary considerably, a typical outer diameter of sheath 6 is 0.86 mm., and the overall length of the instrument, from the tip of the cutting head to the proximal end of the handle, is typically 100 cm.

Figure 1:
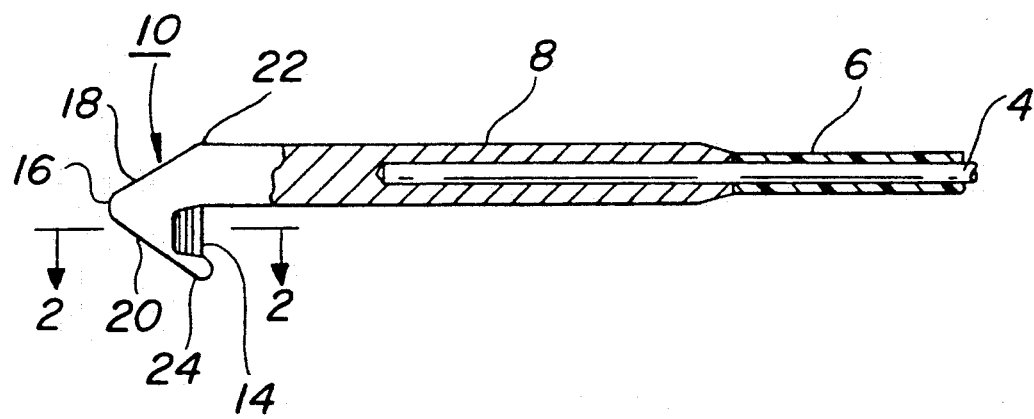
FIG. 1 is a fragmentary elevational view, partly in section of the instrument in accordance with the invention, showing the cutting head at the distal end of the instrument.

The cutting head, as shown in FIG. 1, comprises a shaft 8, which receives the distal end of wire 4 in an axial blind passage into which wire 4 is secured both by a suitable cement and by crimping the shaft onto the wire.

Figure 2:
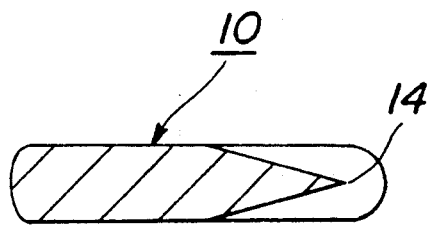
FIG. 2 is a sectional view taken on plane 2—2 of FIG. 1.
Figure 3:
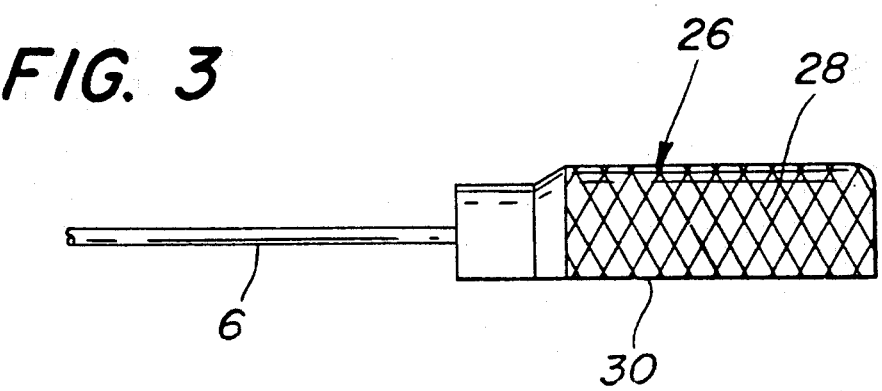
FIG. 3 is a fragmentary elevational view of the proximal end of the instrument, showing the handle.

A laterally extending arm 10 is formed at the distal end of the shaft. Arm 10 is formed with a cutting blade 12 having a proximally facing cutting edge 14 extending transverse to the axis of wire 4, preferably radially. As shown in FIG. 2, arm 10 is comparatively narrow in the direction perpendicular to the plane defined by blade edge 14 and the axis of wire 4.

The cutting head has a blunt tip 16, which is formed by tapering the head in the plane defined by the blade edge 14 and the axis of wire 4, i.e. the plane of FIG. 1. The tip 16 is radially offset from the axis of wire 4. The cutting head has two edges 18 and 20, which extend in oblique directions relative to the axis of wire 4, and which form an acute angle with each other. Edges 18 and 20 can be straight or nearly straight, and in any event have radii of curvature (in the plane defined by the blade edge and the wire axis) which are greater than the radius of curvature of tip 16. Edges 18 and 20 extend forwardly toward tip 16 from locations 22 and 24 which are adjacent to the ends of the blade edge 14. At these locations, the radii of curvature are smaller than the radii of curvature of edges 18 and 20. A bulbous element is formed at location 24, and extends slightly in the proximal direction relative to the blade edge.

At the opposite end of wire 4, a handle 26 is secured by a suitable cement. This handle has a knurled gripping surface 28 in the form of a part (e.g. 270°) of a circular cylinder. A flat 30 is formed on the handle in a plane perpendicular to the plane defined by blade edge 14 and the axis of wire 4. This flat enables the surgeon to know the orientation of the cutting blade even though it is hidden within a vein.

In a typical use, the instrument is introduced through an incision near the patient's ankle into the saphenous vein, while an angioscope, i.e. a flexible endoscope, is introduced into the same vein at thigh level. The cutting head of the instrument is passed up through the vein toward the point at which the angioscope is introduced. A clear saline solution is introduced through an irrigation channel in the angioscope to clear the field of view through the angioscope of blood. The introduction of saline solution causes closure of the valve in the vein just below the point of introduction of the angioscope. When the cutting head of the valvulotome passes through this valve, it is visible through the angioscope, and its position and orientation can be controlled by the handle of the valvulotome so that it is positioned to engage the valve cusps. The valve cusps are cut, typically by several passes of the cutting head at different orientations, while the cutting is monitored through the angioscope. When cutting of the uppermost saphenous valve is completed, the valvulotome is withdrawn while the angioscope is moved further into the vein to follow the cutting head to the location of the next valve. The valves are cut sequentially under direct monitoring through the angioscope until the entire vein is opened and usable as an arterial by-pass.

The tapered design of the cutting head allows the valvulotome to pass upwardly through the vein more easily than was possible with conventional single blade, retrograde valvulotomes, and with less chance of damage to the wall of the vein or to its branches. At the same time, the flattened design of the head, as seen in FIG. 2, makes the orientation of the cutting blade easy to determine by viewing the cutting end of the valvulotome through a fiberoptic angioscope. The tapered configuration of the valvulotome cutting head also tends to center the cutting blade in the vein, thereby reducing the tendency of the end of the cutting head to become engaged in side branches of the vein.

While a specific version of the valvulotome has been described, it should be understood that numerous modifications can be made. For example, while Nickel-Titanium alloy is a desirable material for wire 4, other materials can be used, including coil spring wires. Coatings other than PTFE can be used, such as hydrophilic coatings, and the wire can even be used uncoated. The shape of the cutting head can vary somewhat from the shape shown in FIGS. 1 and 2, and the angle between edges, while preferably acute but approaching 90°, can be greater or less than the angle shown. Many other modifications can be made to the invention without departing from the scope of the invention as defined in the following claims.

I claim:

1. A valvulotome for surgically incising venous valves in situ in order to convert a vein into an arterial bypass, comprising a thin, elongated, flexible wire having distal and proximal ends and having a centrally located axis, a cutting head secured to the distal end of the wire for passing through the vein in either direction, said cutting head having a single, narrow arm in fixed relationship with the wire and extending laterally from said axis, said arm having a blade edge facing in the proximal direction and extending in a direction transverse to said axis, and said cutting head also having a blunt tip edge offset from said axis projecting in the distal direction and tapered edges continuously and smoothly connected between said tip edge and lateral edges adjacent to the ends of said blade edge, said tapered edges extending in opposite directions which are oblique relative to said axis and forming an acute angle with each other in a plane defined by said blade edge and by said axis when said wire is straight, said tip edge and said lateral edges all having radii of curvature shorter than the radii of the curvature of said tapered edges in said plane; whereby the cutting head tends to center in the vein and pass through a venous valve in either direction with ease and less chance for trauma.

2. A valvulotome according to claim 1 in which the lengths of the radii of curvature of said tapered edges are such that said tapered edges are substantially straight.

3. A valvulotome according to claim 1 in which said head has a blunt element located adjacent to the end of said blade edge farthest from said axis, with at least a portion of said blunt element extending proximally relative to said end of the blade edge.

4. A valvulotome according to claim 1 in which said wire is composed of a Nickel-Titanium alloy.

5. A valvulotome according to claim 1 in which said wire is composed of a Nickel-Titanium alloy, and is coated with polytetrafluoroethylene.

6. A valvulotome according to claim 1 in which the maximum dimension of said head in the direction perpendicular to said plane is less than the maximum dimension of said head in the direction parallel to said blade edge.

* * * * *